(12) United States Patent
Kumar

(10) Patent No.: US 10,010,500 B2
(45) Date of Patent: Jul. 3, 2018

(54) CERAMIC IMPLANTS AFFORDING CONTROLLED RELEASE OF ACTIVE MATERIALS

(75) Inventor: Mukesh Kumar, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 2039 days.

(21) Appl. No.: 12/195,789

(22) Filed: Aug. 21, 2008

(65) Prior Publication Data

US 2010/0047318 A1 Feb. 25, 2010

(51) Int. Cl.
- A61K 9/00 (2006.01)
- A61K 9/14 (2006.01)
- A61K 38/18 (2006.01)
- A61K 9/50 (2006.01)

(52) U.S. Cl.
CPC .......... *A61K 9/0024* (2013.01); *A61K 9/5031* (2013.01)

(58) Field of Classification Search
None
See application file for complete search history.

(56) References Cited

U.S. PATENT DOCUMENTS

| | | |
|---|---|---|
| 3,929,971 A | 12/1975 | Roy |
| 4,976,736 A | 12/1990 | White et al. |
| 5,344,654 A | 9/1994 | Rueger et al. |
| 5,366,507 A | 11/1994 | Sottosanti |
| 5,543,156 A | 8/1996 | Roorda et al. |
| 5,545,409 A | 8/1996 | Laurencin et al. |
| 5,626,861 A | 5/1997 | Laurencin et al. |
| 5,648,097 A | 7/1997 | Nuwayser |
| 5,885,829 A | 3/1999 | Mooney et al. |
| 6,033,582 A * | 3/2000 | Lee et al. ................. 216/37 |
| 6,180,606 B1 | 1/2001 | Chen et al. |
| 6,224,893 B1 | 5/2001 | Langer et al. |
| 6,331,312 B1 | 12/2001 | Lee et al. |
| 6,334,891 B1 | 1/2002 | Constantz et al. |
| 6,376,573 B1 | 4/2002 | White et al. |
| 6,417,247 B1 | 7/2002 | Armstrong et al. |
| 6,454,811 B1 | 9/2002 | Sherwood et al. |
| 6,630,155 B1 | 10/2003 | Chandrashekar et al. |
| 6,692,738 B2 | 2/2004 | MacLaughlin et al. |
| 6,716,444 B1 | 4/2004 | Castro et al. |
| 7,078,032 B2 | 7/2006 | MacLaughlin et al. |
| 7,166,570 B2 | 1/2007 | Hunter et al. |
| 7,931,683 B2 * | 4/2011 | Weber ................. A61L 31/088 623/1.42 |
| 2002/0169066 A1 | 11/2002 | Cassidy et al. |
| 2003/0083741 A1 | 5/2003 | Woo et al. |
| 2004/0002770 A1 | 1/2004 | King et al. |
| 2005/0107870 A1 | 5/2005 | Wang et al. |
| 2005/0155779 A1 | 7/2005 | Wang et al. |
| 2006/0121084 A1 | 6/2006 | Borden et al. |
| 2006/0142853 A1 | 6/2006 | Wang et al. |
| 2006/0199876 A1 * | 9/2006 | Troczynski et al. .......... 523/115 |
| 2006/0233849 A1 | 10/2006 | Simon et al. |
| 2006/0233851 A1 | 10/2006 | Simon et al. |
| 2007/0027532 A1 | 2/2007 | Wang et al. |
| 2007/0123973 A1 | 5/2007 | Roth et al. |
| 2008/0306584 A1 * | 12/2008 | Kramer-Brown ............. 623/1.39 |

FOREIGN PATENT DOCUMENTS

| | | | |
|---|---|---|---|
| WO | WO 97/46178 | 12/1997 | |
| WO | 00/45734 | * 8/2000 | ............... A61F 2/00 |
| WO | WO 00/45734 | 8/2000 | |

OTHER PUBLICATIONS

Bhardwaj et al ("In vitro evaluation of Poly(D,L-lactide-co-glycolide) polymer-based implants containing the αL-melanocyte stimulating hormone analog, Melanotan-I," Journal of Controlled Release 45 (1997) 49-55).*

Bubb, D. et al. "Resonant infrared pulsed laser deposition of thin biodegradable polymer films" Appl. Phys. A 74, pp. 123-125. Published Oct. 17, 2001.

Deonarine, et al. "Gene Expression Profiling of Cutaneous Wound Healing" Journal of Translational Medicine, vol. 5, No. 11 (11 pages) 2007.

Favez et al. "RF-Plasma Deposition and Surface Characterization of a Biodegradable Thin Film Coating" European Cells and Materials, vol. 3, Suppl. 1, pp. 20-21 (2002).

Jung, Y. et al. "Characterization of Surface-Modified Poly(DL-lactide-co-glycolide) Scaffolds from Hydrophilic Monomers using Plasma-Enhanced CVD" J. Ind. Eng. Chem., vol. 11, No. 1, pp. 165-169 (2005).

Mercado, A. et al. "Pulsed laser deposition vs. matrix assisted pulsed laser evaporation for growth of biodegradable polymer thin films" Appl. Phys. A 81, pp. 591-599. Published Sep. 30, 2004.

Panchalingam et al. "Molecular surface tailoring of biomaterials via pulsed RF plasma discharges" J. Biomater. Sci. Polymer Edn, vol. 5, No. 1/2, pp. 131-145 (1993).

Susut, C. et al. "Plasma enhanced chemical vapor depositions to encapsulate crystals in thin polymeric films: a new approach to controlling drug release rates" International Journal of Pharmaceutics 288, pp. 253-261 (2005).

Van der Zee, M. "Biodegradability of Polymers—Mechanisms and Evaluation Methods". Chapter 1 (pp. 1-31) from Handbook of Biodegradable Polymers, C. Bastioli, ed. Rapra Technology Limited (2005).

* cited by examiner

*Primary Examiner* — Robert T. Crow
*Assistant Examiner* — John P Nguyen
(74) *Attorney, Agent, or Firm* — Schwegman Lundberg & Woessner, P.A.

(57) ABSTRACT

Implantable compositions providing release of bioactive agents according to a predetermined release profile and methods for their use. Such compositions include at least one ceramic substrate; a bioactive substance loaded on a surface of the ceramic substrate forming a loaded surface zone operable to release said bioactive substance according to a release profile under physiological conditions; and a biodegradable polymer having an in vivo degradation period, forming a continuous or discontinuous coating on an area of the ceramic substrate.

13 Claims, 1 Drawing Sheet

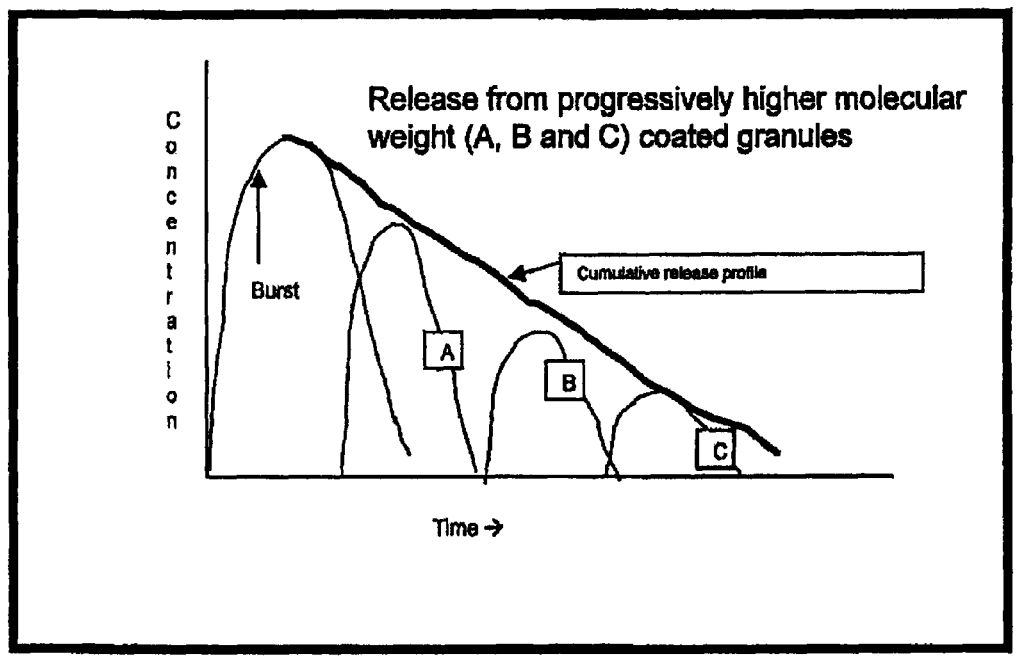

CERAMIC IMPLANTS AFFORDING CONTROLLED RELEASE OF ACTIVE MATERIALS

BACKGROUND

The present technology relates to implantable compositions that exhibit desired release profiles of bioactive agents.

Various approaches have been employed in attempting to provide implantable compositions that provide systemic or local delivery of drug actives. Some active technologies, e.g., insulin pumps, have been developed to provide variable rate drug delivery. However, these require specialized equipment and are desirable for use in only chronic conditions. Alternatively, passive drug releasing implants have been developed to provide a post-implantation burst or spike of the active agent after in vivo biodegradation of a long-term coating. Many such approaches simply provide long-term release at a constant rate. However, among other issues, these materials can exhibit premature release of the bioactive agent through the layer of long-term biodegradable coating. Therefore, it would be advantageous to provide implants capable of releasing bioactive agents in a manner that is more selective, with decreased risk of premature release, and that is adaptable to provide any of various pre-selected drug release profiles.

SUMMARY

The present technology provides implants that are capable of releasing bioactive agents in a manner that offers improved selectivity, with decreased risk of premature release, and that are adaptable to provide any of various pre-selected drug release profiles.

The present technology provides, for example, implantable drug delivery compositions comprising: (a) at least one ceramic substrate; (b) a bioactive substance loaded on a surface of a said ceramic substrate forming a loaded surface zone operable to release said bioactive substance according to a release profile under physiological conditions; and (c) a biodegradable polymer having an in vivo degradation period, forming a continuous or discontinuous coating on an area of a said ceramic substrate; wherein the composition comprises at least two said loaded surface zones having different release profiles, or at least two said coatings having different in vivo degradation periods. The compositions may comprise a plurality of ceramic substrates, such as microspheres, that are particles having a diameter of about 1 to about 50 μm. The composition may comprise at least three loaded surfaces having different release profiles, or at least three coatings having different in vivo degradation periods.

DRAWINGS

The present technology will become more fully understood from the detailed description and the accompanying drawing.

FIG. 1 presents an illustration of a "decreasing rate" drug release profile from a composition comprising uncoated, active agent-loaded substrate, as well as three different coated, active agent-loaded substrates, wherein the three different coatings comprise different molecular weights of the same biodegradable polymer.

It should be noted that the figure set forth herein is intended to exemplify the general characteristics of materials and methods among those of the present technology. This figure may not precisely reflect the characteristics of any given embodiment, and is not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. The following definitions and non-limiting guidelines must be considered in reviewing the description of the technology set forth herein.

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The citation of references herein does not constitute an admission that those references are prior art or have any relevance to the patentability of the technology disclosed herein. All references cited in the "Description" section of this specification are hereby incorporated by reference in their entirety.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. "A" and "an" as used herein indicate "at least one" of the item is present; a plurality of such items may be present, when possible.

In various embodiments, an implantable composition is provided that comprises a set of coated, loaded ceramic substrates or zones. Each of the coatings comprises a layer of biodegradable polymer that is applied over all or part of the surface of a loaded ceramic substrate. The ceramic substrate is loaded in that it comprises bioactive agent(s) deposited on its surface. Such loading can be present in all or part of the surface of a ceramic substrate. A layer of biodegradable polymer is applied over (on or sealed atop) a loaded substrate or over at least part (a zone) of the loaded surface thereof. At least two different coatings are present, and the coated substrates, or zones thereof, may be loaded with the same or different bioactive agent(s). The coatings of the set are selected to provide different in vivo biodegradation periods for different coatings, thereby allowing release, from the implanted composition, of bioactive agent(s) according to a desired release profile over time at the implant site.

Ceramic Substrates

A ceramic substrate can comprise any ceramic useful in medical implants, including glasses or ceramics comprising mono-, di-, tri-, α-tri-, β-tri-, and tetra-calcium phosphate, hydroxyapatite, calcium sulfates, calcium oxides, calcium carbonates, magnesium calcium phosphates, phosphate glass, bioglass, and mixtures thereof. In various embodiments, the ceramic substrate comprises PRO OSTEON (coral hydroxyapatite, from Interpore Cross Int'l, Inc.), or CALCIGEN PSI (resorbable bone graft substitute, from Biomet, Inc.). Ceramics among those useful herein are described in U.S. Patent Application Publications 2006/0233851, Simon et al, published Oct. 19, 2006; and 2006/0233849, Simon et al, published Oct. 19, 2006; both of which are incorporated by reference herein.

A ceramic substrate can be a monolithic or porous solid ceramic. A macroscopic ceramic substrate can be used, and in some embodiments, a plurality of zones on the surface thereof can be provided as loaded, coated zones having different coating biodegradation periods. Smaller substrates can be used, such as ceramic particles (e.g., granules or microspheres), a plurality of which can be treated to provide loaded, coated substrates having different coating biodegradation periods. A combination of different substrates can be used, wherein the resulting composition is designed to exhibit, upon implantation, at least two, and in some embodiments at least three, different coating biodegradation periods.

Bioactive Agents

Bioactive agents useful herein include organic molecules, proteins, peptides, peptidomimetics, nucleic acids, nucleoproteins, antisense molecules, polysaccharides, glycoproteins, lipoproteins, carbohydrates and polysaccharides, botanical extracts, and synthetic and biologically engineered analogs thereof, living cells (other than adipose stromal cells) such as chondrocytes, bone marrow cells, viruses and virus particles, natural extracts, and combinations thereof. Specific non-limiting examples of bioactive materials include hormones, antibiotics and other antiinfective agents, hematopoietics, thrombopoietics, agents, antidementia agents, antiviral agents, antitumoral agents (chemotherapeutic agents), antipyretics, analgesics, antiinflammatory agents, antiulcer agents, antiallergic agents, antidepressants, psychotropic agents, anti-parkinsonian agents, cardiotonics, antiarrythmic agents, vasodilators, antihypertensive agents, diuretics, anti-cholinergic, antidiabetic agents, anticoagulants, cholesterol lowering agents, gastrointestinal agents, muscle relaxants, therapeutic agents for osteoporosis, enzymes, vaccines, immunological agents and adjuvants, cytokines, growth factors, cellular attractants and attachment agents, gene regulators, vitamins, minerals and other nutritionals, nutraceuticals and combinations thereof. Bioactive agents useful herein, and methods for loading ceramic substrates with such agents, include those described in U.S. Patent Application Publication 2007/0123973, Roth et al., published May 31, 2007, incorporated by reference herein.

Some examples of useful bioactive agents include cytokines, including isolated, synthetic or recombinant molecules. Cytokines useful herein include growth factors such as transforming growth factor (TGF-beta), bone morphogenic proteins (BMP, BMP-2, BMP-4, BMP-6, and BMP-7), neurotrophins (NGF, BDNF, and NT3), fibroblast growth factor (FGF), granulocyte-colony stimulating factor (G-CSF), granulocyte-macrophage colony stimulating factor (GM-CSF), nerve growth factor (NGF), neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), vular endothelial growth factor (VEGF), epidermal growth factor (EGF), insulin-like growth factors (IGF-I, IFG-II), and combinations thereof.

In some embodiments, the bioactive agent(s) can comprise antimicrobials, such as aminoglycosides, ansamycin, carbacephems, carbapenems, cephalosporins, glycopeptides, macrolides, monobactams, oxazolidinones, nitrofurans, penicillin, polypeptides, quinolones, sulfonamides, or tetracycline antibiotics. In various embodiments, the bioactive agent comprises a tetracycline, a rifampin, or mixtures thereof, for example a combination of minocycline, and rifampin.

In some embodiments, the bioactive agent can be provided in any of various stages of purification. Thus, the active can be provided in neat form, or in the form of, e.g., fully or partially demineralized bone matrix, a cell lysate fraction, or a racemic mixture, provided that whatever form is selected is a physiologically acceptable form.

Biodegradable Polymer Layers

Biodegradable polymers useful herein include any physiologically acceptable polymers that exhibit total in vivo biodegradation within a time frame useful, in sound medical judgment, for providing therapeutic efficacy. For example, in some embodiments, any physiologically acceptable polymer can be used that exhibits total in vivo biodegradation of a 1 mm-thick, ceramic-applied layer thereof in 12 months or less.

Some examples of useful biodegradable polymers include: polyhydroxyalkanoates, such as PGA, PLA, PHB, PHV, PHH, PHO; polylactones including polylactides, i.e. polydilactones, such as, PPL, PBL, PVL, PCL; and their copolymers, such as PLGA, PHBV, and the like. In some embodiments, PLGA can be used. Biodegradable polymers among those useful herein are described in U.S. Patent Application Publications 2006/0121084, Borden et al., published Jun. 8, 2006; 2006/0233851, Simon et al, published Oct. 19, 2006; and 2006/0233849, Simon et al, published Oct. 19, 2006; all of which are incorporated by reference herein. Such copolymers can be 50:50 mole percent lactide: glycolide residues or more, e.g., 75:15 or 85:15.

As used herein, various polymer terms have the following meanings: polyglycolide (PGA); polylactide (PLA), typically poly-D,L-lactide; poly-L-lactide (PLLA); poly-D,L-lactide (PDLLA); poly(D,L-lactide-co-glycolide) (PLGA); poly-hydroxybutyrate (PHB), typically poly-3-hydroxybutyrate; poly-hydroxyvalerate (PHV), typically poly-3-hydroxyvalerate; poly(hydroxybutyrate-co-hydroxyvalerate) (PHBV); poly-hydroxyhexanoate (PHH); poly-hydroxyoctanoate (PHO); poly-propiolactone (PPL), typically poly-beta-propiolactone; poly-butyrolactone (PBL), typically poly-gamma-butyrolactone; poly-valerolactone (PVL), typically poly-delta-valerolactone; and poly-caprolactone (PCL), typically poly-epsilon-caprolactone.

The materials for and thicknesses of the layers in a particular embodiment of the composition can be selected to provide a desired release profile for the bioactive agent therefrom. Release profiles can be, e.g.: pulsed (e.g., varying between zero release and a positive release rate), spiked (e.g., varying between low and high positive release rates), steadily increasing or decreasing, or constant, or any combination thereof. In some embodiments, the release profile can exhibit repeating features, and in some embodiments, these can be periodic, e.g., regularly periodic.

For any given biodegradable polymer, the layer thickness can be selected to provide release at completion of the biodegradation period for that layer. Some examples of useful biodegradation periods include: 6- or 12-hours, 1-, 2-, or 3-days, 1-, 2,-, 4, or 8-weeks and so forth.

The materials for and thickness of a given layer of polymer deposited upon the loaded substrate can be selected based on resorption criteria described, e.g., in U.S. Patent Application Publication 2006/0233849, Simon et al, published Oct. 19, 2006. A given layer can be, e.g., from about 0.05 µm to about 5 mm, more typically from about 0.1 µm to about 1 mm. In various embodiments, a layer can be from about 0.5 to about 750 µm, or more typically from about 1 to about 500 µm.

In selecting a layer thickness for its degradation period, useful thicknesses for common polyhydroxyalkanoate (PHA) or polylactide polymers include, e.g.: (1) from about 1 to about 30 µm for 6-hour release, or typically from about 1 to about 10 µm; (2) from about 3 to about 50 µm for 12-hour release, or typically from about 3 to about 25 µm; (3) from about 5 to about 100 µm for 24-hour release, or typically from about 5 to about 50 µm; and (4) from about 45 to about 750 µm for 7-day release, or typically from about 45 to about 350 µm.

Table 1 illustrates selected layer thicknesses that can be used to match desired release profiles for some common biodegradable polymers.

TABLE 1

Some Typical Polymer Layer Thicknesses (µm)

| Polymer | Desired Degradation Period | | | | |
|---|---|---|---|---|---|
| | 6 h | 12 h | 1 d | 7 d | 2 wk |
| PLLA | 1 | 3 | 6 | 45 | 90 |
| PDLLA | 3 | 6 | 12 | 90 | 180 |
| PGA | 5 | 10 | 20 | 150 | 300 |
| PLGA 85:15 | 10 | 20 | 40 | 250 | 500 |

Thus, e.g., where a pulsed release profile is desired at 12 hours, 1 day, and 7 days, from a composition in which the polymer layers comprise PLLA, three separate layers of about 3, 6, and 45 µm could be present.

Factors that impact the selection of the thickness of a biodegradable polymer layer can include the chemical identity, molecular weight, and degree of crystallinity of the polymer, the nature of the bioactive agent, and the in vivo environment of the target site into which the composition is to be implanted. For example, in some embodiments, chemically different polymers having different biodegradation rates can be selected for use in different layers having different biodegradation periods. In some embodiments, lower and higher molecular weight forms of a chemically identical polymer can be used in different layers, i.e. on different substrates or on different, loaded substrate surface zones, to provide different biodegradation periods. Where the natures of the polymers provide different biodegradation periods, in some embodiments, the different layers can be about the same thickness. For example, three different loaded zones or substrates can each be coated with about 90 µm of PLGA 85:15, PDLLA, or PLLA, respectively, so as to provide a composition, comprising the three, that exhibits biodegradation periods of about 2.5 days, 7 days, and 2 weeks, respectively.

The choice of biodegradable polymer can be based on an assessment of polymers' biodegradation rates. Biodegradation rates can be determined by use of any technique known useful in the art therefor, including in vivo test implantation in animal models, and in vitro contact with or colonization by eukaryotic or prokaryotic cell cultures. Useful techniques are also described, e.g., in C. Bastioli, ed., *Handbook of Biodegradable Polymers* (2005) (Rapra Technology, UK) (see chapter 1, section 1.5 "Measuring Biodegradation of Polymers").

In various embodiments, uncoated, loaded zone(s) or substrate(s) can also be present in the composition to further provide an immediate release dose from the composition. Alternatively, or in addition, in some embodiments, the biodegradable polymer matrix of the layer can further comprise a bioactive agent(s), the same as or different from the one to be released upon completion of the layer's biodegradation period. For a given drug, this option can provide one release rate that differs from the release rate upon completion of the layer's biodegradation period.

Methods of Preparation

In various embodiments, a composition hereof can be prepared by providing at least one macroscopic ceramic substrate or a plurality of smaller ceramic substrates. All or part of the surface of the substrate(s) is then loaded with a desired biological agent(s) or combination thereof. For example, the biological agent can be applied in the form of an aqueous solution or suspension. This can be applied to a surface or surface zone of the substrate, as by painting, or the substrate can be immersed in the solution or suspension. The active agent-applied substrate is then dried, e.g., under ambient conditions, under vacuum, or by lyophilization, to provide a loaded substrate.

The selected polymer layer can be deposited on the loaded substrate using a vapor deposition or related technique. Vacuum sublimation, laser-assisted evaporation, thermal spraying, pulsed laser deposition, and the like can be used. However, in various embodiments, a vapor or plasma deposition technique can be used, such as a physical vapor deposition, plasma deposition, reactive plasma deposition, chemical vapor deposition, plasma-assisted or plasma-enhanced chemical vapor deposition technique. In various embodiments, a vapor deposition technique can be used. In some alternative embodiments, a solution deposition or related technique, e.g., in situ polymerization, can be used. Details for such vapor deposition, solution deposition, and related processes are described, e.g., in Panchalingam et al., "Molecular surface tailoring of biomaterials via pulsed RF discharge," *J. Biomaterials Science Polymers* 5, 131-145, 1993; Timmons et al., "Plasma enhanced chemical vapor deposition to encapsulate crystals in thin polymeric films: a new approach to controlling drug releasing rates," *International J of Pharmaceutics* 288 (2005), 253-261; Bubb et al., "Resonant Infrared pulsed laser deposition of thin biodegradable polymer films," *Appl. Phy. A*74, 123-125, 2002; and Ratner et al., "RF Plasma Deposition and surface characterization of a biodegradable thin film coatings," *European Cells and Materials*, Vol 3, Supl 1, 2002, p 20-21.

In various embodiments, the surface of the monolithic or porous substrate can comprise pores defined by walls and struts. In various embodiments, a vapor-deposited polymer layer can contact at least 90%, about or at least 95%, or about or at least 97%, 98%, or 99% or more of the loaded ceramic surface, or coated zone thereof. Where the ceramic substrate comprises a pore-bearing surface, the vapor-deposited polymer layer can exhibit that degree of contact with the surface area, including with the ceramic pore walls and struts of the substrate zone/surface that it coats. A solution-deposited or otherwise formed polymer layer can be provided that exhibits a similar degree of contact with the coated zone/surface, including its surface features.

The resulting composition comprises at least one such multi-zone-coated, loaded substrate or a combination of different single-zone-coated or fully-coated, loaded substrates. Thus, the resulting composition can be provided in the form of a rigid solid, such as an orthopedic prosthesis, or in the form of a dry plug or powder capable of being hydrated to form a plastic plug, or a plastic putty, gel, or paste, such as a bone paste. Hydration can be performed prior to implantation, utilizing any physiologically acceptable liquid, e.g., water, saline, plasma, platelet-rich plasma, whole blood, et al. The fluid can be one that is autologous to the subject to receive the implant. The composition can alternatively be provided in the form of a hydrated plug, putty, gel, or paste.

In various embodiments, a composition that comprises a combination of different single-zone-coated or fully-coated, loaded substrates, such as single-zone-coated or fully-coated, loaded ceramic particles, can further comprise other ingredients known in the art as useful in contact or admixture with the implant materials. Thus, various additives, such as plasticizing agents, processing aids (e.g., binders and/or lubricants), storage aids (e.g., preservatives, antioxidants, and/or dryness-promoting agents); rehydration aids, such as wetting-facilitation agents; alginate; and the like. Typically, such agents can constitute less than 20%, preferably about 15% or less, or about 10% or less, or about 5% or less, or about 4% or less, or about 3% or less, or about 2% or less, or about 1% or less of the composition.

Useful examples of plasticizing agents include: powdered demineralized bone matrix, preferably powdered human or bovine DBM; one or more polyether, such as a cellulose derivative, e.g., methylcellulose, carboxymethylcellulose, ethylcellulose, hydroxyethylcellulose, hydroxypropyl methylcellulose, cellulose acetate butyrate, salts thereof, and combinations thereof; and alcohols and polyols of at least three carbon atoms in length, e.g., oleyl alcohol, glycerol, sorbitol, xylitol, propylene glycol, butylene glycol, polyethylene glycol, and vinyl alcohols (polyvinylalcohols). In some embodiments, a cellulose derivative can be used as the plasticizer in a plasticizing-agent-containing embodiment hereof.

Kits

The present technology also provides kits that contain a sterile composition hereof with instructions for use as an implant, or where the composition is provided in dry, e.g., lyophilized form, with instructions for hydrating the composition and for using the hydrated composition as an implant, e.g., as a bone graft material.

Methods of Use

An implantable composition can be used, for example, to provide an alternating time course of in vivo release of two or more different bioactive substances, such as two or more different classes of antibiotics. This strategy can be particularly useful in preventing establishment of an infection at the implantation site by permitting disuse of one antibiotic so as to allow, e.g., spontaneous ejection from microbes of an antibiotic resistance plasmid therefor. However, in carrying out such a strategy, it can be important to eliminate or minimize the degree of premature release of a coated second antibiotic during scheduled release of a first. Eliminating or minimizing such premature release avoids exposing bacteria or other infectious agents simultaneously to a mixture of antibiotics, thereby helping to avoid development of multiple resistance in such bacteria or agents that can occur by retention and accumulation of different antibiotic resistance plasmids. Thus, improved selectivity of drug release can be a useful feature for enhancing the efficacy of therapy.

Various embodiments of compositions hereof, e.g., compositions comprising vapor-deposited biodegradable polymer layers, can provide improved selectivity of release of bioactive agents, and so are particularly useful in such methods.

In various embodiments, a composition hereof can be used to enhance wound healing. For example, factors involved in early (e.g., through day 2) and late (e.g., days 4-8) wound healing stages can be selectively released at those stages in order to foster healing at the site of implantation. See, e.g., K. Deonarine et al., *Journal of Translational Medicine* 5:11 (Feb. 21, 2007) (doi:10.1186/1479-5876-5-11), describing such factors.

The compositions and methods of the present technology are exemplified in the following non-limiting Examples.

EXAMPLE 1

Granules of Calcigen PSI (Biomet Manufacturing Corp., Warsaw, Ind., US) are exposed a concentrated aqueous solution of Gentamicin sulfate. After the porous structure is soaked with the solution, the granules are retrieved from the antibiotic solution and left to dry. The dried and antibiotic loaded granules are placed in a RF plasma chamber and coated with a resorbable polymer similar to that described by Panchalingam et al., "Molecular surface tailoring of biomaterials via pulsed RF discharge," *J Biomaterials Science Polymers* 5, 131-145, 1993; Timmons et al., "Plasma enhanced chemical vapor deposition to encapsulate crystals in thin polymeric films: a new approach to controlling drug releasing rates," *International J of Pharmaceutics* 288 (2005), 253-261; Bubb et al., "Resonant Infrared pulsed laser deposition of thin biodegradable polymer films," *Appl. Phy.* A74, 123-125, 2002; and Ratner et al., "RF Plasma Deposition and surface characterization of a biodegradable thin film coatings," *European Cells and Materials*, Vol 3, Supl 1, 2002, p 20-21. Alternatively, a solution of the choice polymer may be made in a solvent that will not dissolve the antibiotic. The antibiotic loaded granules are then exposed to this solution and eventually extracted. The granules are allowed to dry to form a skin of the polymer on the struts of the porous network of the Calcigen PSI granules. The process is optionally repeated to buildup the polymer. Examples of polymer that can be employed to coat the granules are PLLA, PGA, PLLA-PGA, polyallyl alcohol and others.

EXAMPLE 2

The method described above is repeated to coat Calcigen PSI granules with gentamicin sulfate. After the drying operation, the granules are exposed to a concentrate solution of refampin and minocycline in alcohol. This exposure does not alter the loading of gentamicin sulfate in Calcigen PSI, as gentamicin sulfate is not soluble in alcohol. The granules are extracted from the alcohol solution and allowed to dry. The granule are placed in a chamber and coated with a resorbable polymer (PLLA-PGA) using any of the methods described in [1 -4].

To alter the drug elution profile, either or a combination of the following can be employed—(i) the coating thickness is modified (ii) higher molecular weight polymer is employed (iii) a polymer with a stearic group that protects a cleaving bond to hydrolytic attack (i.e. PLLA a opposed to PGA). The coating thickness can be increased by allowing the coating to build up with increased exposure in the plasma chambers.

To tailor the drug elution profile of the system, a composition may comprise antibiotic loaded granules coated with different concentrations of the antibiotic. Such a composition will allow different intensity of "burst" and "trailing" elution in vivo. Similar effects can be achieved by designing dose where there are antibiotic loaded granules are coated with polymers of different thickness or molecular weights.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

The release characteristics of one embodiment of such a composition is illustrated in FIG. 1. The composition comprises amounts of uncoated granules (for "burst" effect) as well as granules with polymer coating of increasing molecular weight (A, B, C, etc., in FIG. 1.) Further, the ceramic may be exposed to drug solution of different concentrations, thus providing a means of altering the amount of drug that can be delivered by the granules. Upon implantation, the uncoated granules immediately release the drug producing the burst effect and then the lower molecular weight (i.e., A., FIG. 1) release their supply as this polymer degrades. The granules with intermediate molecular weight polymer coating release next, followed by release from the granules with higher molecular weight coatings. This successive release results in a cumulative release profile similar to that shown in FIG. 1. As seen, to alter the cumulative profile, the molecular weight of the vapor deposited resorbable polymer and the total quantity of any kind of coated granules can be so adjusted that the curves A, B, C, etc., can overlap or be well separated.

What is claimed is:

1. An implantable drug delivery composition comprising:
   a set of ceramic microsphere substrates including at least a first substrate and a second substrate, each substrate comprising:
   (A) a loaded surface zone formed of a bioactive substance loaded on a surface of said ceramic substrate, the loaded surface zone operable to release said bioactive substance according to a release profile under physiological conditions; and
   (B) a coating formed on an area of the loaded surface zone of said ceramic substrate, the coating being formed of a biodegradable polymer having an in vivo degradation period;
   wherein the coatings of the first substrate and the second substrate differ in at least one of polymer type, molecular weight, thickness, and combinations thereof such that the coatings of the first substrate and the second substrate have different in vivo degradation periods such that cumulative release of the composition of said bioactive substance varies according to the release profile.

2. The composition according to claim 1, wherein the composition comprises substrates having coatings with at least three different in vivo degradation periods.

3. The composition according to claim 1, wherein the coating of the first substrate exhibits an in vivo degradation period of 1 to about 7 days and the coating of the second substrate exhibits an in vivo degradation period of about 1 to 4 weeks.

4. The composition according to claim 1, wherein the coating of at least one of the first substrate and the second substrate exhibits an in vivo degradation period of about 2 to 8 weeks.

5. The composition according to claim 1, wherein coating is discontinuous and the composition comprises a substrate wherein an area of the loaded surface zone is not coated with the biodegradable polymer.

6. The composition according to claim 1, wherein the ceramic substrate comprises any of the physiologically acceptable hydroxyapatites, calcium phosphates, calcium sulfates, or combinations thereof.

7. The composition according to claim 1, wherein the biocompatible, biodegradable polymer comprises any of the physiologically acceptable polylactides, polyhydroxyalkanoates, copolymers thereof, or combinations thereof.

8. The composition according to claim 7, wherein the biocompatible, biodegradable polymer comprises PLA, PGA, or PLGA, or any combination thereof.

9. The composition according to claim 1, wherein the biocompatible, biodegradable polymer coating is from about 1 μm to about 500 μm thick.

10. The composition according to claim 1, wherein the bioactive substance comprises a pharmaceutically acceptable polypeptide.

11. The composition according to claim 1, wherein the bioactive substance is present in or on the surface of the ceramic substrate in an amount that is from about 0.01 to about 100 pg per $mm^2$ of the area of the loaded surface zone loaded therewith.

12. The composition according to claim 1, wherein the set of said ceramic substrates exhibits a smoothly decreasing in vivo drug release profile.

13. The composition according to claim 1, wherein the set of said ceramic substrates exhibits an increase-decrease profile of in vivo drug release.

* * * * *